United States Patent
Eder et al.

(10) Patent No.: US 9,117,257 B2
(45) Date of Patent: Aug. 25, 2015

(54) METHOD TO PREPARE AN INTERVENTIONAL AND/OR DIAGNOSTIC IMAGING PROCEDURE WITH AT LEAST TWO DIFFERENT MEDICAL IMAGING MODALITITES

(71) Applicants: Hanns Eder, Bubenreuth (DE); Patrick Gross, Ismaning (DE); Annemarie Hausotte, Erlangen (DE); Martin Ringholz, Erlangen (DE); Eva Rothgang, Nuerngberg (DE)

(72) Inventors: Hanns Eder, Bubenreuth (DE); Patrick Gross, Ismaning (DE); Annemarie Hausotte, Erlangen (DE); Martin Ringholz, Erlangen (DE); Eva Rothgang, Nuerngberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/173,205

(22) Filed: Feb. 5, 2014

(65) Prior Publication Data
US 2014/0219525 A1 Aug. 7, 2014

(30) Foreign Application Priority Data
Feb. 5, 2013 (DE) .......................... 10 2013 201828

(51) Int. Cl.
*G06F 19/00* (2011.01)
*G06T 7/00* (2006.01)
*A61B 6/00* (2006.01)

(52) U.S. Cl.
CPC ............ *G06T 7/0012* (2013.01); *A61B 6/5217* (2013.01); *A61B 6/5247* (2013.01); *G06F 19/34* (2013.01); *G06T 2207/30004* (2013.01)

(58) Field of Classification Search
CPC ..................... G06T 2207/30004; G06F 19/34
See application file for complete search history.

(56) References Cited

U.S. PATENT DOCUMENTS

| | | | |
|---|---|---|---|
| 2007/0118399 A1* | 5/2007 | Avinash et al. | 705/2 |
| 2007/0237371 A1* | 10/2007 | Zhu et al. | 382/128 |
| 2008/0107313 A1* | 5/2008 | O'Dea | 382/128 |
| 2010/0191541 A1* | 7/2010 | Prokoski | 705/2 |
| 2013/0188852 A1 | 7/2013 | Bakai et al. | |

\* cited by examiner

Primary Examiner — Utpal Shah
(74) Attorney, Agent, or Firm — Schiff Hardin LLP

(57) ABSTRACT

In a method and medical imaging system to prepare an interventional and/or diagnostic imaging procedure to be conducted with at least two different medical imaging modalities of the system, a patient is positioned on a patient support device and the patient support device, together with the patient, are moved into a patient acquisition region of a first medical imaging modality of the system. A first image data set of the patient to be examined is acquired with the first medical imaging modality. The first image data set is automatically evaluated in a data evaluation unit. At least patient parameter is automatically calculated from the evaluated first image data set. At least one compatibility value is automatically calculated depending on the at least one patient parameter and depending on at least one apparatus parameter of at least one additional medical imaging modality in the system. The compatibility value indicates whether the additional modality is compatible with the patient in order to conduct another of the procedures using that additional modality.

12 Claims, 1 Drawing Sheet

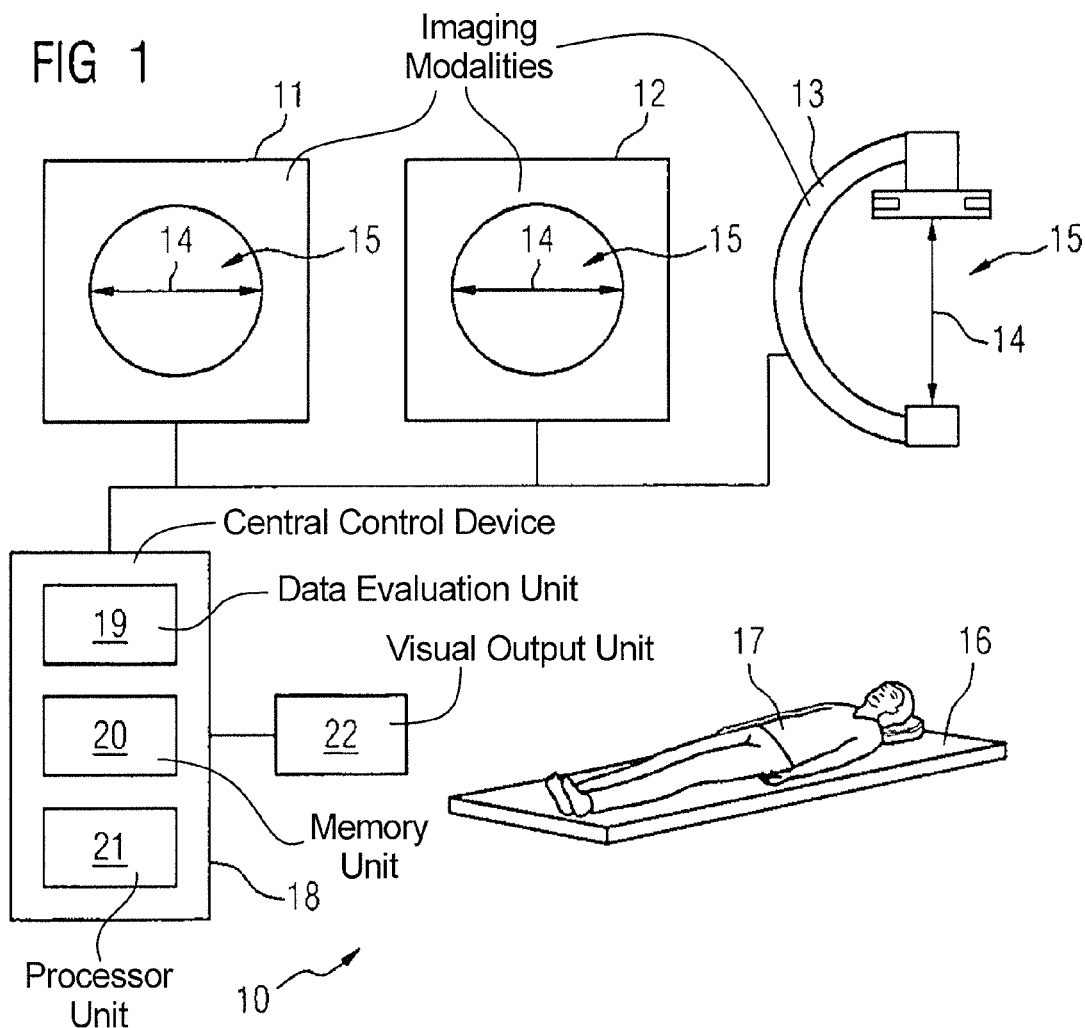
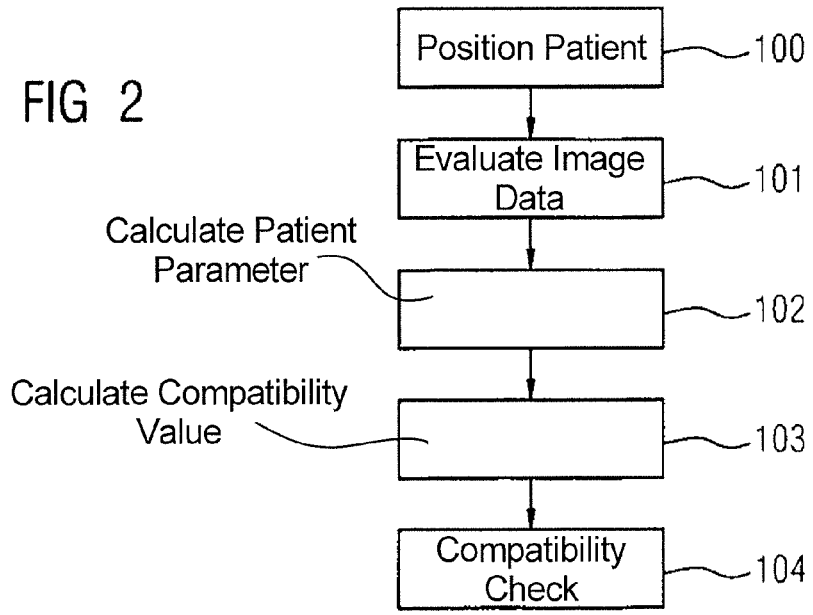

METHOD TO PREPARE AN INTERVENTIONAL AND/OR DIAGNOSTIC IMAGING PROCEDURE WITH AT LEAST TWO DIFFERENT MEDICAL IMAGING MODALITITES

BACKGROUND OF THE INVENTION

1. Field of the Invention

The present invention concerns a method for preparing an interventional and/or diagnostic imaging procedure performed with a medical imaging system that has at least two different medical imaging modalities.

2. Description of the Prior Art

For interventional and/or diagnostic imaging, procedures performed on the patient and/or for treatment of the patient, the procedures are prepared and/or planned at least in part using medical image information that has been acquired by one or more medical imaging modalities, for example a magnetic resonance apparatus, a computed tomography apparatus, a PET (positron emission tomography) apparatus, etc. For this purpose, a reproducible, exact position of the patient is required in order to be able to fuse and/or combine image information of different medical imaging modalities to prepare and/or plan the intervention. However, these different medical imaging modalities frequently have different dimensions of the patient receptacle region provided for receiving the patient therein.

For interventional and/or diagnostic imaging, the patient is positioned on a patient support device for a medical imaging examination. The position of the patient on the patient support device should be adapted to the different imaging modalities, in particular to the different dimensions of the acquisition region provided for the acquisition of the patient, so that unwanted collisions of the patient with a housing of the medical imaging modality that surrounds the acquisition region can be prevented.

In the positioning of the patient, the medical technician does not always succeed in taking into account all medical imaging modalities provided for the interventional and/or diagnostic imaging. Most often, the medical operator only learns whether the arrangement of the patient on the patient support device is sufficient for a collision-free introduction into the additional medical imaging modalities during the insertion process into the corresponding medical imaging modality. However, this can lead to a repositioning of the patient if an additional imaging measurement (data acquisition) is to take place with an additional medical imaging modality. However, a repositioning of the patient hinders a fusing and/or superposition of image information and/or image data of the different medical imaging modalities. In addition to this, the clinical workflow can be significantly disrupted and/or delayed, for example during a neurosurgical procedure on the head of a patient, wherein the head is clamped within a head mounting and is covered with sterile cloths.

SUMMARY OF THE INVENTION

An object of the present invention is to provide a method that simplifies preparation for an interventional and/or diagnostic imaging.

The invention concerns a method for a preparation of an interventional and/or diagnostic imaging procedure with at least two different medical imaging modalities, with the following steps:

position a patient on a patient support device and introduce the patient support device, together with the patient, into a patient acquisition region of a first medical imaging modality, acquire a first image data set of the patient to be examined with the first medical imaging modality, evaluate the first image data set in a data evaluation unit, calculate at least one patient parameter from the evaluated first image data set, and calculate at least one compatibility value depending on the at least one patient parameter and depending on at least one apparatus parameter of at least one additional medical imaging modality.

The acquired image data of the first image data set can be used both for a medical analysis and for compatibility considerations and/or plausibility considerations for examinations of the patient with additional medical imaging modalities (which are of a different design from the first medical imaging modality). Compatibility between the patient and the additional medical imaging modalities (in particular those that are of a different design from the first medical imaging modality) can be detected in such a manner, and this information can be used for the additional preparation and/or examination of the interventional and/or diagnostic imaging. In this context, a patient parameter is a parameter and/or a value of a physical property of the patient and/or of a partial region of the patient that is to be examined, for example a parameter and/or a value of a geometric dimension and/or a density, etc. Furthermore, an apparatus parameter is an apparatus-specific parameter and/or value of the additional medical imaging modality (that is of a different design from the first medical imaging modality). The apparatus parameter can be a parameter and/or a value of a geometric dimension of an opening of a patient acquisition region and/or a detection type, etc. A compatibility value is a value that designates a compatibility of the patient (represented by the patient parameter) with the apparatus parameter of the additional medical imaging modality (that is of a different design from the first medical imaging modality) for the acquisition of an additional medical image data set. The patient support device preferably is a bed table on which the patient is borne and that can be introduced into a patient receptacle region of the medical imaging modality. Furthermore, the patient support device can include additional support aids, for example a head mount and/or supports and/or underlays for the targeted positioning of the patient in an examination position on the bed table.

Furthermore, the patient parameter can include at least one item of information of at least one volume element of the patient with regard to a property (in particular a physical property) of the patient, so a particularly efficient and reliably significance of the compatibility value can be achieved.

The property of the patient advantageously includes the density of the volume element of the patient. Additional information with regard to foreign bodies and/or implants within the partial region of the patient that is to be examined can enter into the compatibility considerations. For example, a smaller selection of additional medical imaging modalities for the acquisition of an additional image data set is available for patients with a cardiac pacemaker and/or a metal implant.

Alternatively or additionally, the property of the patient can include an outer contour of the volume element of the patient, in particular of a partial region of the patient that is relevant to the medical examination. Compatibility of the patient with regard to his or her contour can be determined for the additional available medical imaging modalities. In addition, possible collisions of the patient with the additional available medical imaging modalities can already be indicated using the compatibility value. For example, the outer contour can be determined by means of a segmentation algorithm.

A subject size, for example the patient together with the patient support device, can be determined particularly quickly by identifying an envelope of all outer contours of different volume elements. An exact dimension of the patient positioned on the patient support device can be obtained in such a manner, and therefore a particularly reliable conclusion as to the compatibility value can be achieved.

In a further embodiment of the invention, a selection of the additional medical imaging modalities that are compatible with the patient parameter is provided using the at least one compatibility value. An additional procedure to prepare the interventional and/or diagnostic imaging and the interventional and/or diagnostic imaging itself can be determined particularly quickly in such manner by a medical operator (a physician, for example). For example, time-consuming preparations of the patient for examinations with an additional medical imaging modality that is not compatible with the patient parameter can be prevented, and/or the patient can be positioned and/or prepared such that compatibility of the patient with an additional medical imaging modality that is precluded from the selection can be achieved.

An additional communication of information to the medical operator can be achieved if the selection of the additional medical imaging modalities that are compatible with the patient parameter is presented visually by means of an output unit. The optical output unit can be a monitor and/or a touchscreen and/or additional optical output units that appear to be reasonable to those skilled in the art.

The at least one compatibility value can include a collision probability of the patient (or of the patient together with the patient support device) with a housing of the at least one additional medical imaging modality, the housing surrounding the patient acquisition region. A possible risk of collision of the patient with the additional medical imaging modality (in particular with the housing surrounding the patient acquisition region) can already be determined in such a manner before an additional medical imaging examination. The patient thus can be protected against a possible collision with the additional medical imaging modality, and thus against injury.

A particularly efficient and reliable calculation of a collision probability of the patient positioned on the patient support device with the additional medical imaging modality, in particular a housing surrounding the patient acquisition region, can be achieved if the apparatus parameter includes a geometric dimension of an opening of the patient acquisition region of the additional medical imaging modality for the calculation of the at least one compatibility value. Alternatively or additionally, the apparatus parameters for the calculation of the at least one compatibility value can include the type of acquisition of a medical image data set and/or additional apparatus-specific parameters and/or values that are relevant to the acquisition of medical image data sets.

The invention also encompasses a medical imaging system with at least two different imaging modalities and a control device that has a data evaluation unit, wherein the medical imaging system is designed to implement a method as described above. The acquired image data of the first image data set can be used both for a medical analysis and for compatibility considerations and/or plausibility considerations for examinations of the patient with additional medical imaging modalities (in particular those that are of a design different than that of the first medical imaging modality). Compatibility between the patient and the additional medical imaging modalities (in particular those that are of a design different than that of the first medical imaging modality) can be detected in such a manner, and this information can be used for the additional preparation and/or examination of the interventional and/or diagnostic imaging.

The above object also is achieved in accordance with the present invention by a non-transitory, computer-readable data storage medium encoded with programming instructions that, when the storage medium is loaded into a computerized control and evaluation system of a medical imaging system that has at least two different imaging modalities, causes the control and evaluation system to operate the imaging system in accordance with one or more of the embodiments of the method described above.

BRIEF DESCRIPTION OF THE DRAWINGS

FIG. 1 schematically illustrates a medical imaging system according to the invention.

FIG. 2 is a flowchart of the method according to the invention regarding a preparation of an interventional and/or diagnostic imaging with at least two different medical imaging modalities.

DESCRIPTION OF THE PREFERRED EMBODIMENTS

A medical imaging system 10 according to the invention is shown in FIG. 1. The medical imaging system 10 has multiple medical imaging modalities 11, 12, 13 that can be differentiated with regard to a detection type to acquire medical image data sets and/or with regard to a dimensioning given the same detection type. For example, the individual medical imaging modalities 11, 12, 13 can be formed by a magnetic resonance device, a computed tomography device, a PET device, an angiography device, etc. In addition, the individual medical imaging modalities 11, 12, 13 can be formed only by magnetic resonance devices, for example, wherein the individual magnetic resonance devices can be differentiated with regard to a magnetic field strength and/or an opening diameter 14 of a patient acquisition region 15 and/or additional parameters that are meaningful to those skilled in the art.

The medical imaging system 10 furthermore has at least one patient support device 16 on which a patient 17 is supported for a medical imaging examination, and that can be introduced into a patient acquisition region 14 in one of the medical imaging modalities 11, 12, 13. In the exemplary embodiment, the at least one patient bearing device is designed such that it can be introduced without collision into at least some of the different medical imaging modalities 11, 12, 13. In principle, the medical imaging system 10 can have multiple patient support devices 16, with each of the patient support devices 16 being provided for introduction of the patient 17 into only a respective one of the medical imaging modalities 11, 12, 13. In addition to a bed table that can be introduced into a patient acquisition region 14, the patient support device 16 can include additional positioning aids, for example a head mount, supports and/or underlays for targeted positioning of the patient 17 in an examination position on the bed table. Furthermore, the medical imaging system 10 has a control device. In the exemplary embodiment, the control device is formed as a central control device 18 that has a data evaluation unit 19, a memory unit 20 and a processor unit 21. The central control device 18 can additionally include further units that appear to be reasonable to those skilled in the art.

The medical imaging system 10 may have multiple decentralized control devices 18 that each include a data evaluation unit 19, a memory unit 20 and a processor unit 21, wherein the respective control devices 18 being individually associated with respective ones of the medical imaging modalities 11, 12, 13 of the medical imaging system 10.

The control device 18 with the data evaluation unit 19 is designed for a central data evaluation of medical image data that are acquired by means of the different medical imaging modalities 11, 12, 13. For this purpose, the medical imaging system 10 has a data transfer unit (not shown in detail) that transfers acquired image data of the individual medical imaging modalities 11, 12, 13 to the control device 18.

To prepare for an interventional and/or diagnostic imaging of a patient 17, multiple medical image data sets—in particular of the partial region of the patient 17 that is relevant to the interventional and/or diagnostic imaging—are acquired with different medical imaging modalities 11, 12, 13. An optimally exact 3D image of the partial region of the patient that is relevant to the interventional and/or diagnostic imaging is created by means of the data evaluation unit 18 from the different data sets of the different medical imaging modalities 11, 12, 13.

A method to prepare an interventional and/or diagnostic imaging with at least two different medical imaging modalities 11, 12, 13 is shown in detail in FIG. 2. In a positioning step 100, the patient 17 is initially positioned by a medical operator (a physician, for example) on the patient bearing device 16 and prepared for the interventional and/or diagnostic imaging.

In the positioning step 100, the patient 17 (together with the patient bearing device 16) is subsequently introduced into the patient acquisition region 15 of a first of the medical imaging modalities 11, 12, 13.

In a following method step 101, a first image data set is acquired by means of the first medical imaging modality 11, 12, 13 and transferred to the data evaluation unit 19 of the control device 18 by means of the data transfer unit. In an evaluation step 102 that follows the method step 101, the image data of the first image data set is evaluated by the data evaluation unit 19. In a following additional method step 102, at least one patient parameter is calculated from the evaluated image data. The patient parameter preferably includes at least one item of information with regard to a property of at least one volume element of the patient 17. The information with regard to the property of at least one volume element of the patient 17 can include a value and/or parameter of an optical density of the volume element, and/or a value and/or parameter of an outer contour of the volume element of the patient 17, and/or additional patient parameters obtained from the first image data set. Additional subjects within the patient (for example a cardiac pacemaker etc.) can be concluded using the optical density determined from the evaluated image data.

If the patient parameter includes an outer contour of a volume element and/or a partial region of the patient 17, this patient parameter is determined by the data evaluation unit 19 through the use of segmentation algorithms, for example. In addition, in the additional method step 102 an envelope for all calculated outer contours can be determined by the data evaluation unit 19 from the individual outer contours of different volume elements. This envelope represents the patient 17, or the partial region of the patient 17, that is relevant to the examination on the patient bearing device 16, wherein the envelope corresponds to a subject size and/or a patient size of the patient 17 or of the partial region of the patient 17. In addition to the outer contour of the patient 17, the envelope can include an outer contour of the patient support device 16 or which the patient 17 currently is placed. The information of the outer contour of the patient support device 16 can also be determined by the data processing unit 19 from the first image data set and/or can be read out from a database that is stored in the memory unit 20. In simplified form, the outer contour of the patient support device 17 (in particular of a support table that can be introduced within the patient acquisition regions 15 of the different medical imaging modalities 11, 12, 13) can include a rectangular area.

In an additional evaluation step 103, at least one compatibility value is calculated by the data evaluation unit 19 depending on the calculated patient parameter of the patient 17 and depending on at least one apparatus parameter of an additional one of the medical imaging modalities 11, 12, 13. The apparatus parameter of the additional medical imaging modality preferably includes an (in particular apparatus-specific) parameter and/or value that, for example, includes a geometric dimension (in particular an opening diameter 14) of an opening of the patient acquisition region 15 and/or a detection type etc. of the additional medical imaging modality 11, 12, 13. The additional medical imaging modality 11, 12, 13 is of different design than the first medical imaging modality 11, 12, 13.

A selection of the additional medical imaging modalities 11, 12, 13 taken into account in the additional evaluation step 103 to calculate the compatibility value can, for example, be conducted manually by a medical operator. Insofar as no special selection and/or manually entered selection of the additional medical imaging modalities 11, 12, 13 is present, at least one compatibility value is calculated by the data evaluation unit 19 in the additional evaluation step 103 for all additional available medical imaging modalities 11, 12, 13.

The calculation of the compatibility value can include a collision probability of the patient 17 positioned on the patient bearing device 16 with a housing surrounding the patient acquisition region 15 of the additional medical imaging modality 11, 12, 13. For example, the patient parameter (formed here as a cross-section of an outer contour or as a cross-section of an envelope of the outer contours of the patient 17) is compared with an apparatus parameter of the additional medical imaging modality, this apparatus parameter designating an opening cross-section 14 of the patient acquisition region 15. Insofar as the cross-section of the outer contours, or the cross-section of the envelope of the outer contours of the patient 17, is smaller than the opening cross-section 14 of the patient acquisition region 15 of the selected additional medical imaging modality 11, 12, 13 and/or the additional available medical imaging modalities 11, 12, 13, the patient parameter is compatible with the apparatus parameter and a positive compatibility value is present.

Insofar as the cross-section of the outer contours, or the cross-section of the envelope of the outer contours of the patient 17, is greater than the opening cross-section 14 of the patient acquisition region 15 of the selected additional medical imaging modality 11, 12, 13 and/or the additional available medical imaging modalities 11, 12, 13, the patient parameter is not compatible with the apparatus parameter and a negative compatibility value is present.

If the patient parameter includes the density of the volume element and/or of a partial region of the patient 17, a compatibility check of the patient parameter with regard to (for example) a material property of the volume element of the patient 17 with the apparatus parameter of the selected additional medical imaging modality 11, 12, 13 and/or the additional available medical imaging modalities 11, 12, 13 takes place in the data evaluation unit 19 in the additional evaluation step 104.

Using the patient parameter, a selection of the additional medical imaging modalities that are compatible with the patient parameter is provided by the data evaluation unit 19 in a provision step 104 following the additional evaluation step 103. In this provision step 104, a visual output of the additional medical imaging modalities 11, 12, 13 that are compatible with the patient parameter also takes place. For this purpose, the medical imaging system 10 has a visual output unit 22 that, for example, is formed by a monitor and/or a touchscreen, etc.

After the visual output of the compatibility values, the medical operator can select a corresponding additional medical imaging modality 11, 12, 13 and the patient can be introduced into the patient acquisition region 15 of the selected additional medical imaging modality 11, 12, 13. A second image data set can be acquired by means of said selected additional medical imaging modality 11, 12, 13, and three-dimensional image data of the patient can be determined from the at least two image data sets in such a manner, and the interventional and/or diagnostic imaging can subsequently be started.

Insofar as no positive compatibility value between the determined patient parameter and the available additional medical imaging modality 11, 12, 13 is determined in the evaluation step 103, a repositioning of the patient 17 on the patient support device 16 can also be conducted by the medical operator, for example in order to avoid collisions between the patient and the housing of the different additional imaging modalities 11, 12, 13, which housing surrounds the patient acquisition region 15, and the method for preparing an interventional and/or diagnostic imaging with at least two different medical imaging modalities can be restarted.

The control device 18 is loaded with the corresponding software and/or computer programs to implement the method to prepare an interventional and/or diagnostic imaging with at least two different medical imaging modalities.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method to prepare an imaging procedure, selected from the group consisting of interventional imaging procedures and diagnostic imaging procedures, to be performed by an imaging system that comprises a first medical imaging modality and at least one additional medical imaging modality that differs from said first imaging modality, said method comprising:

positioning a patient on a patient support device and moving the patient support device with the patient thereon into a medical image data acquisition region of said first medical imaging modality;

operating said first medical imaging modality to acquire an image data set from the patient;

in a processor, automatically evaluating said image data set to obtain an evaluation result;

in said processor, calculating, from said evaluation result, at least one patient parameter;

in said processor, calculating at least one compatibility value dependent on said at least one patient parameter and dependent on at least one apparatus parameter that represents a physical attribute of said at least one additional medical imaging modality, said compatibility value designating a compatibility of said at least one additional medical imaging modality for performing an additional procedure, selected from said group consisting of interventional procedures and diagnostic imaging procedures, on said patient using said at least one additional medical imaging modality; and from said processor, making said at least one compatibility value available as an output in a humanly perceptible form.

2. A method as claimed in claim 1 comprising calculating said at least one patient parameter as at least one item of information that represents a property of the patient in at least one volume element of the patient.

3. A method as claimed in claim 2 comprising calculating said at least one patient parameter with said property of the patient designating a density of said volume element.

4. A method as claimed in claim 2 comprising calculating said patient parameter as an outer contour of said volume element.

5. A method as claimed in claim 4 comprising calculating said patient parameter as a subject size of the patient formed by an envelope of all outer contours of a plurality of different volume elements of the patient.

6. A method as claimed in claim 1 wherein said medical imaging system comprises multiple additional medical imaging modalities, and comprising making a selection of one of said multiple additional medical imaging modalities for conducting said further examination, dependent on said at least one compatibility value.

7. A method as claimed in claim 6 comprising providing a designation of said additional medical imaging modalities that are compatible with said patient parameter as a visual presentation at an output unit connected with said processor.

8. A method as claimed in claim 1 comprising calculating said compatibility value as a collision probability of at least said patient with a housing of said at least one additional medical imaging modality, said housing surrounding a data acquisition region of said at least one additional medical imaging modality.

9. A method as claimed in claim 8 comprising calculating said collision probability of the patient together with said patient support device.

10. A method as claimed in claim 1 wherein said at least one additional medical imaging modality comprises a data acquisition region in which the patient is received therein, said data acquisition region having an opening with a geometric dimension, and calculating said at least one compatibility value using said geometric dimension as said apparatus parameter.

11. A medical imaging system comprising:

a first imaging modality and at least one additional imaging modality, each of said imaging modalities being configured to conduct a procedure selected from the group consisting of interventional procedures and diagnostic imaging procedures on a patient;

a patient support device that receives a patient thereon and moves the patient support device with the patient thereon into a medical image data acquisition region of said first medical imaging modality;

a control unit configured to operate said first medical imaging modality to acquire an image data set from the patient;

a processor configured to automatically evaluate said image data set to obtain an evaluation result;

said processor being configured to calculate, from said evaluation result, at least one patient parameter;

said processor being configured to calculate at least one compatibility value dependent on said at least one patient parameter and dependent on at least one apparatus parameter that represents a physical attribute of said at least one additional medical imaging modality, said compatibility value designating a compatibility of said at least one additional medical imaging modality for performing an additional procedure, selected from said group consisting of interventional procedures and diagnostic imaging procedures, on said patient using said at least one additional medical imaging modality; and said processor being configured to make said at least one compatibility value available as an output in a humanly perceptible form.

12. A non-transitory, computer-readable data storage medium encoded with programming instructions, said data storage medium being loaded into a computerized control and evaluation system of a medical imaging system that comprises a first medical imaging modality and at least one additional medical imaging modality, each of said modalities being configured to perform a procedure selected from the group consisting of interventional procedures and imaging procedures, said programming instructions causing said control and evaluation system to:

operate a patient support device to move the patient support device with the patient thereon into a medical image data acquisition region of said first medical imaging modality;

operate said first medical imaging modality to acquire an image data set from the patient;

evaluate said image data set to obtain an evaluation result;

calculate, from said evaluation result, at least one patient parameter;

calculate at least one compatibility value dependent on said at least one patient parameter and dependent on at least one apparatus parameter that represents a physical attribute of said at least one additional medical imaging modality, said compatibility value designating a compatibility of said at least one additional medical imaging modality for performing an additional procedure, selected from said group consisting of interventional procedures and diagnostic imaging procedures, on said patient using said at least one additional medical imaging modality; and make said at least one compatibility value available as an output in a humanly perceptible form.

* * * * *